United States Patent
Abraham et al.

(10) Patent No.: US 12,390,367 B2
(45) Date of Patent: Aug. 19, 2025

(54) ADJUSTING MOISTURE CONDITIONS FOR OPHTHALMIC LASER ABLATION SURGERY

(71) Applicant: Alcon Inc., Fribourg (CH)

(72) Inventors: Mario Abraham, Burgthann (DE); Michael Wittnebel, Hirschaid (DE)

(73) Assignee: ALCON INC., Fribourg (CH)

( * ) Notice: Subject to any disclaimer, the term of this patent is extended or adjusted under 35 U.S.C. 154(b) by 608 days.

(21) Appl. No.: 17/477,648

(22) Filed: Sep. 17, 2021

(65) Prior Publication Data

US 2022/0096272 A1    Mar. 31, 2022

Related U.S. Application Data

(60) Provisional application No. 63/083,354, filed on Sep. 25, 2020.

(51) Int. Cl.
*A61F 9/008*    (2006.01)
*A61F 9/00*    (2006.01)
*A61F 9/007*    (2006.01)

(52) U.S. Cl.
CPC ........ *A61F 9/00802* (2013.01); *A61F 9/0008* (2013.01); *A61F 9/00745* (2013.01)

(58) Field of Classification Search
CPC .............. A61F 9/0008; A61F 9/00745; A61F 9/00802; A61F 2009/00861
USPC .......................................................... 606/4
See application file for complete search history.

(56) References Cited

U.S. PATENT DOCUMENTS

| | | | |
|---|---|---|---|
| 5,616,139 A * | 4/1997 | Okamoto | A61F 9/008 606/4 |
| 5,971,977 A * | 10/1999 | Korenfeld | A61F 9/008 606/4 |
| 7,090,669 B2 * | 8/2006 | Van Saarloos | A61F 9/00804 606/4 |
| 7,364,575 B2 * | 4/2008 | Van Saarloos | A61F 9/008 606/4 |
| 11,730,627 B2 * | 8/2023 | Abraham | A61F 9/009 606/4 |
| 2008/0039769 A1 * | 2/2008 | Peyman | A61F 9/00827 604/20 |
| 2013/0035672 A1 | 2/2013 | Raksi | |
| 2016/0081851 A1 | 3/2016 | Huang | |
| 2017/0049621 A1 * | 2/2017 | Dick | A61B 18/00 |
| 2017/0340483 A1 | 11/2017 | Rill et al. | |

(Continued)

FOREIGN PATENT DOCUMENTS

| | | |
|---|---|---|
| CN | 1516565 A | 7/2004 |
| CN | 105434104 A | 3/2016 |
| WO | 9412131 A1 | 6/1994 |

*Primary Examiner* — Ahmed M Farah

(57) ABSTRACT

In certain embodiments, an ophthalmic laser ablation system comprises a laser device, liquid remover, and computer. The laser device directs laser radiation towards an eye as a plurality of shots to ablate tissue of the eye according to a treatment pattern. The liquid remover removes liquid from a surface of the tissue of the eye. The computer: determines a moisture maintenance procedure; instructs the liquid remover to remove the liquid from the surface of the tissue at a location of the eye according to the moisture maintenance procedure; and instructs the laser device to ablate the tissue at the location of the eye according to the treatment pattern.

14 Claims, 3 Drawing Sheets

(56) References Cited

U.S. PATENT DOCUMENTS

2022/0062039 A1\* 3/2022 Abraham ............... A61B 3/152
2022/0096272 A1\* 3/2022 Abraham .............. A61F 9/0008

\* cited by examiner

ADJUSTING MOISTURE CONDITIONS FOR OPHTHALMIC LASER ABLATION SURGERY

TECHNICAL FIELD

The present disclosure relates generally to ophthalmic laser ablation systems, and more particularly to adjusting moisture conditions for ophthalmic laser ablation surgery.

BACKGROUND

Laser photoablation, or laser ablation, is the process of removing material from a surface by irradiating it with a laser beam. In ophthalmic surgery, an ablation procedure typically uses an excimer laser to reshape the cornea to change its refractive properties. The excimer laser beam is directed towards the cornea according to a treatment pattern. The beam forces the molecules to detach from each other, and material is removed to yield a desired corneal shape.

There are different types of laser ablation procedures. Laser in-situ keratomileusis (LASIK) involves cutting a flap in the cornea and then using an excimer laser to ablate the cornea. Photo refractive keratectomy (PRK) is similar to LASIK, except instead of creating a flap, the epithelium is removed, e.g., chemically or mechanically.

During laser ablation procedures, the eye is kept open with an eyelid spreader to prevent blinking during the procedure. Tear film naturally protects the eye from damage. Since evaporation of the tear film would lead to loss of the natural protection, the eye is moistened with drops to maintain a liquid film on the eye.

BRIEF SUMMARY

In certain embodiments, an ophthalmic laser ablation system comprises a laser device, liquid remover, and computer. The laser device directs laser radiation towards an eye as a plurality of shots to ablate tissue of the eye according to a treatment pattern. The liquid remover removes liquid from a surface of the tissue of the eye. The computer: determines a moisture maintenance procedure; instructs the liquid remover to remove the liquid from the surface of the tissue at a location of the eye according to the moisture maintenance procedure; and instructs the laser device to ablate the tissue at the location of the eye according to the treatment pattern.

Embodiments may include none, one, some, or all of the following features:

The liquid remover comprises an ultrasonic emitter that generates waves to displace the liquid.

The liquid remover comprises an infrared emitter that generates infrared waves to dry the liquid.

The liquid remover comprises a laser source that generates a laser beam to dry the liquid.

The liquid remover comprises a device that creates a puff of air to dry the liquid.

The moisture maintenance procedure is determined from the treatment pattern.

The liquid is removed prior to each shot or a sequence of shots.

The ophthalmic laser ablation system further comprises a liquid dispenser that applies liquid onto the surface of the tissue. The computer further instructs the liquid dispenser to apply liquid onto the surface of the tissue at the location of the eye according to the moisture maintenance procedure.

The liquid dispenser comprises a sprayer that sprays liquid onto the surface of the tissue.

The liquid dispenser comprises a cannula that disposes liquid onto the surface of the tissue.

The liquid is applied after each shot or a sequence of shots.

The removed liquid is reapplied onto the surface of the tissue at the location of the eye.

A liquid with a strong cooling effect or a liquid for wound healing is applied. Alternatively, a liquid with a strong cooling effect is applied, and then a liquid for wound healing is applied.

In certain embodiments, a method for ophthalmic laser ablation includes: directing, by a laser device, laser radiation towards an eye as a plurality of shots to ablate tissue of the eye according to a treatment pattern; removing, by a liquid remover, liquid disposed outwardly from a surface of the tissue of the eye; and performing the following with a computer: determining a moisture maintenance procedure; instructing the liquid remover to remove the liquid disposed outwardly from the surface of the tissue at a location of the eye according to the moisture maintenance procedure; and instructing the laser device to ablate the tissue at the location of the eye according to the treatment pattern.

Embodiments may include none, one, some, or all of the following features:

The moisture maintenance procedure is determined from the treatment pattern.

A liquid dispenser applies liquid onto the surface of the tissue. The computer instructs the liquid dispenser to apply liquid onto the surface of the tissue at the location of the eye according to the moisture maintenance procedure.

The removed liquid is reapplied onto the surface of the tissue at the location of the eye.

A liquid with a strong cooling effect, and then a liquid for wound healing is applied.

In certain embodiments, an ophthalmic laser ablation system comprises a laser device, liquid remover, liquid dispenser, and computer. The laser device directs laser radiation towards an eye as a plurality of shots to ablate tissue of the eye according to a treatment pattern. The liquid remover removes liquid from a surface of the tissue of the eye. The liquid dispenser applies liquid onto the surface of the tissue. The computer: determines a moisture maintenance procedure from the treatment pattern; instructs the liquid remover to remove the liquid disposed outwardly from the surface of the tissue at a location of the eye according to the moisture maintenance procedure, the liquid prior removed to each shot or a sequence of shots; instructs the laser device to ablate the tissue at the location of the eye according to the treatment pattern; and instructs the liquid dispenser to apply more liquid onto the surface of the tissue at the location of the eye according to the moisture maintenance procedure, the liquid applied after each shot or a sequence of shots. The applying more liquid comprises: applying a liquid with a strong cooling effect; reapplying the removed liquid onto the surface of the tissue at the location of the eye; and applying a liquid for wound healing.

DESCRIPTION OF EXAMPLE EMBODIMENTS

Figure 1:
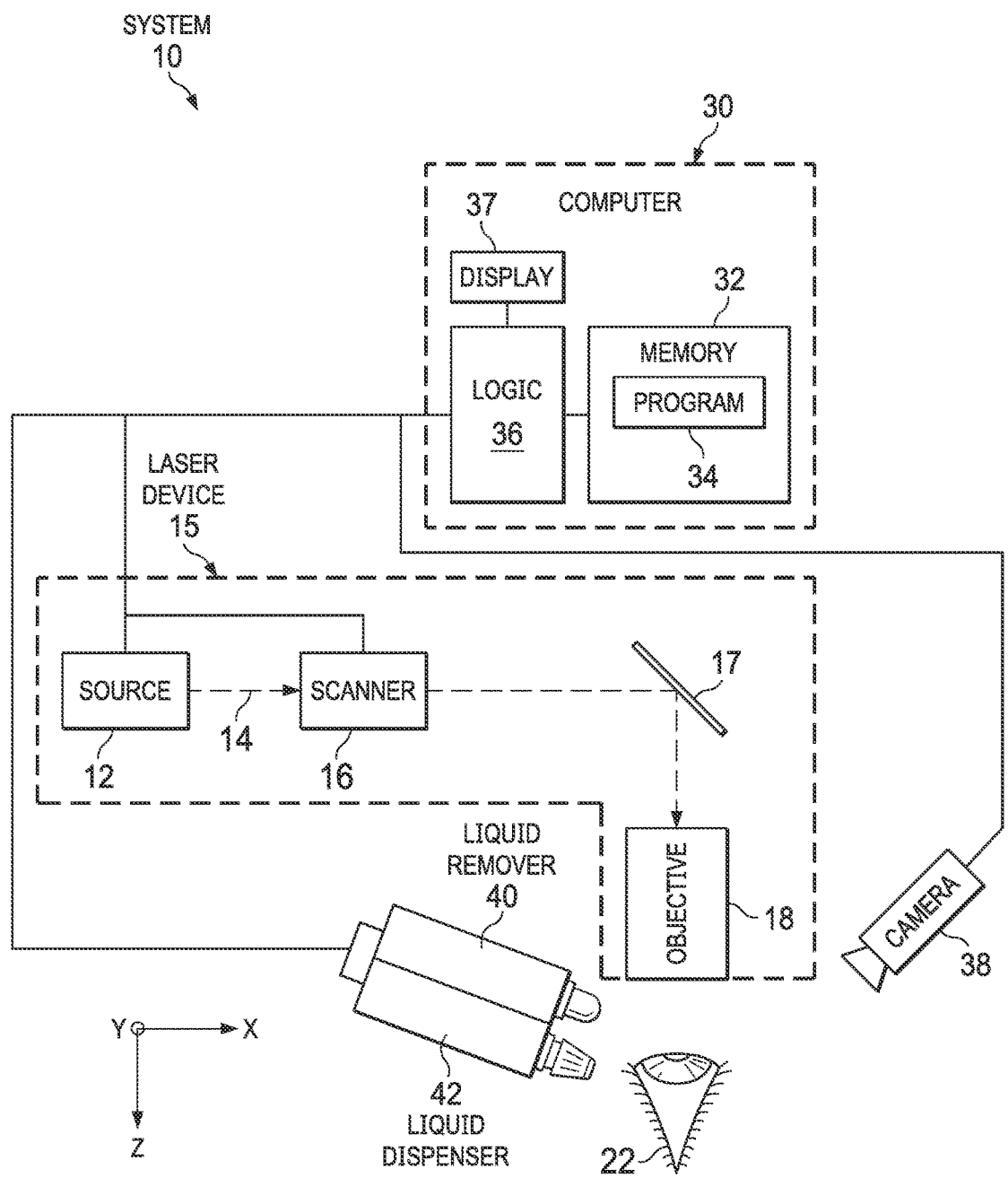
FIG. 1 illustrates an example of an ophthalmic laser ablation system that adjusts the moisture conditions at a target eye.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

During laser ablation procedures, the eye is moistened with drops to maintain a liquid film on the eye. However, the liquid can disrupt the energy influx of the laser beam. As the beam passes through the liquid, energy is lost before the beam can ablate the tissue. Embodiments of the description address this issue by removing at least some of the liquid just prior to ablation to avoid the reduction of energy, and then applying more liquid after ablation to protect the eye.

FIG. 1 illustrates an example of an ophthalmic laser ablation system 10 that adjusts the moisture conditions at a target eye 22 while ablating the tissue of eye 22 according to certain embodiments. In the illustrated example, system 10 includes a laser device 15, a camera 38, a liquid remover 40, a liquid dispenser 42, and a control computer 30, coupled as shown. Laser device 15 includes controllable components, such as a laser source 12, a scanner 16, one or more optical elements 17, and/or a focusing objective 18, coupled as shown. Computer 30 includes logic 36, a memory 32 (which stores a computer program 34), and a display 37, coupled as shown. For ease of explanation, the following xyz-coordinate system is used: The z-direction is defined by the propagation direction of the laser beam, and the xy-plane is orthogonal to the propagation direction. Other suitable xyz-coordinate systems may be used.

As an overview, computer 30 instructs components of system 10 to adjust the moisture conditions at eye 22 according to the following example of operation to allow the laser beam of laser device 15 to perform a procedure on eye 22 according to a treatment pattern. In the example, laser device 15 is configured to direct laser radiation towards eye 22 as laser shots to ablate tissue of eye 22 according to the treatment pattern. Liquid remover 40 is configured to remove liquid disposed outwardly from a surface of the tissue of the eye, and liquid dispenser 42 is configured to apply more liquid onto the surface of the tissue. Computer 30 determines a moisture maintenance procedure. Computer 30 then instructs the components to: remove the liquid disposed outwardly from the tissue at a location of the eye according to the moisture maintenance procedure; ablate the tissue at the location according to the treatment pattern; and apply more liquid to the tissue at the location according to the moisture maintenance procedure.

Turning to the parts of system 10, laser source 12 generates a laser beam that ablates tissue of eye 22 according to a treatment pattern. Laser source 12 may be an excimer laser that generates a laser beam with a wavelength of less than 300 nm. A treatment pattern may be a shot pattern that defines x, y (and perhaps z) coordinates for shot positions at which laser radiation pulses are to be directed. The treatment pattern may be determined from an ablation profile, which indicates the volume of tissue to be removed at particular x, y positions of the cornea. Given the volume of tissue ablated per pulse, the number of pulses to be directed at an x, y position can be readily calculated from the volume of tissue defined by the ablation profile.

Scanner 16 laterally and longitudinally directs the focal point of the laser beam. The lateral direction refers to directions orthogonal to the direction of beam propagation, i.e., the x, y directions. Scanner 16 may laterally direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam.

The longitudinal direction refers to the direction parallel to the laser beam propagation, i.e., the z-direction. Scanner 16 may longitudinally direct the laser beam in any suitable manner. For example, scanner 16 may include a longitudinally adjustable lens, a lens of variable refractive power, or a deformable mirror that can control the z-position of the beam focus. The components of scanner 16 may be arranged in any suitable manner along the beam path, e.g., in the same or different modular units.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Camera 38 records images of the eye 22 through patient interface 20. Examples of camera 38 include a video, an optical coherence tomography, or an eye-tracking camera. Camera 38 delivers image data, which represent recorded images of the eye 22, to computer 30. Computer 30 may carry out image processing on the image data to identify the amount of liquid disposed onto eye 22. The image processing includes recognizing the liquid in the recorded images and determining the amount of the liquid.

Liquid remover 40 removes liquid disposed outwardly from the surface of eye 22. The liquid may include lacrimal fluid (i.e., tears) and liquid previously applied to eye 22. Liquid dispenser 42 applies more liquid to the surface of eye 22. Liquid dispenser 42 may apply any liquid suitable for an eye procedure, e.g., a saline and/or lacrimal liquid. The liquid may include additions, such as medication (e.g., pain reducer), coolant, disinfectant (e.g., antibacterial), and/or volatile ingredient (e.g., alcohol). Liquid remover 40 and liquid dispenser 42 are described in more detail with reference to FIG. 2.

Computer 30 controls components of system 10 in accordance with computer program 34. For example, computer 30 controls components (e.g., laser source 12, scanner 16, optical elements 17, and/or focusing objective 18) to focus the laser beam of laser device 15 at eye 22 and to ablate at least a portion of eye 22 according to a treatment pattern. To successfully treat eye 22, eye 22 should have the appropriate moisture conditions. To appropriately moisten eye 22, computer 30 instructs the components to remove and apply liquid to eye 22 according to a moisture maintenance procedure.

The moisture maintenance procedure may have any suitable steps performed in any suitable order, consecutively or concurrently. For example, the procedure may remove liquid prior to one or more shots and/or apply liquid after one or more shots. As another example, the procedure may simultaneously remove liquid from an area that is the next to be ablated and apply liquid to other areas that are not the next to be ablated.

The moisture maintenance procedure may remove any suitable portion of the liquid. For example, the procedure may remove liquid only in the area of the next shot, the area of the next shot plus a surrounding area, some of the area of laser ablation, or all of the area of laser ablation. As another example, the procedure may remove only some of the liquid in an area or may remove all of the liquid in an area.

The moisture maintenance procedure may apply liquid in any suitable manner. For example, the procedure may apply new liquid from a reservoir. As another example, the procedure may remove liquid from the eye and then reapply the removed liquid to the eye, such that the liquid is reused. As another example, the procedure may move liquid from one area of the eye to another area of the eye, without removing and reapplying the liquid. As another example, the procedure apply different types of liquid, such as a liquid with a stronger cooling effect (e.g., a highly volatile liquid) or a liquid for wound healing (e.g., protective or medicinal liquid). As another example, the procedure may change the type of applied liquid, such as first apply a liquid with a stronger cooling effect and then apply a liquid for wound healing.

The moisture maintenance procedure may have steps that yield more (or less) moisture during particular parts of a procedure. For example, steps that yield more moisture may apply more liquid than liquid that is removed, and/or apply liquid more frequently than removing liquid. Steps that yield less moisture may apply less liquid than liquid that is removed, and/or apply liquid less frequently than removing liquid.

Computer 30 may determine the moisture maintenance procedure in any suitable manner. Computer 30 may retrieve the moisture maintenance procedure from a memory 32 of computer 30. In certain embodiments, computer 30 may determine the moisture maintenance procedure from the treatment pattern such that the procedure is customized for the pattern. For example, if the pattern has an area that needs more moisture (e.g., a higher density of ablation shots), the procedure may include steps for the area that yield more moisture. In certain embodiments, computer 30 may use machine learning or artificial intelligence to adjust the procedure. For example, computer 30 may detect, via images from camera 28, that an area needs more moisture, and may adjust the procedure to apply more liquid to the area.

In certain embodiments, computer 30 performs the moisture maintenance procedure to appropriately moisten eye 22. Computer 30 may perform the procedure in any suitable manner. For example, computer 30 may remove the liquid disposed outwardly from the tissue prior to each shot or prior to a sequence of shots of the plurality of shots. As another example, computer 30 may apply more liquid to the tissue at the location after each shot or after a sequence of shots of the plurality of shots.

Figure 2:
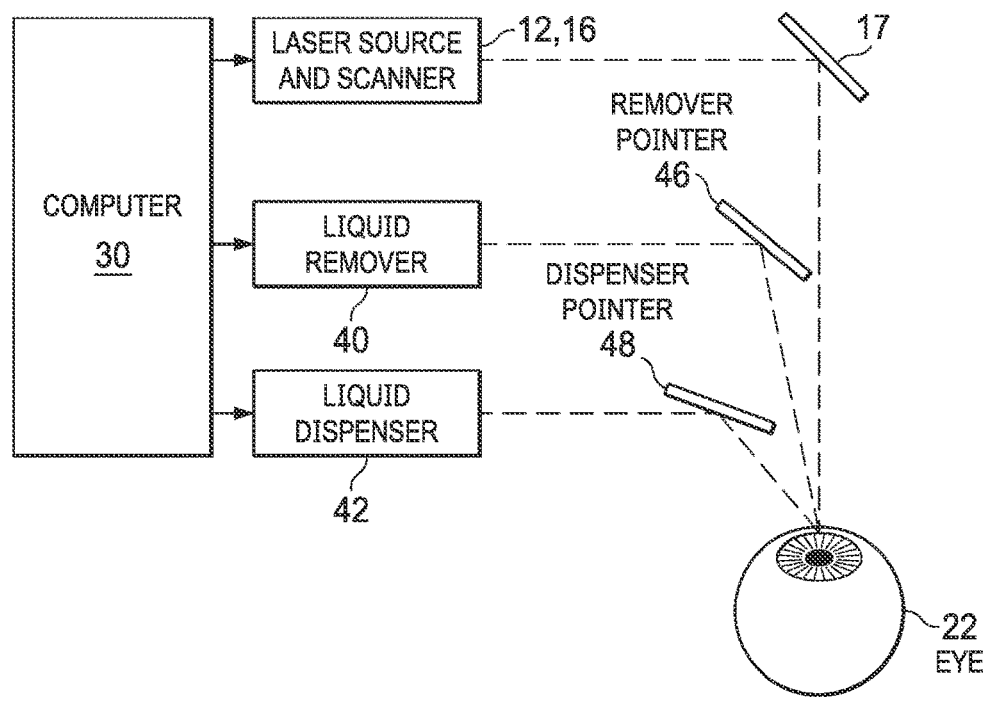
FIG. 2 illustrates examples of a liquid remover and a liquid dispenser that may be used in the system of FIG. 1.

FIG. 2 illustrates examples of liquid remover 40 and liquid dispenser 42 that may be used in system 10 of FIG. 1. In the illustrated example, liquid remover 40 includes a remover pointer 46, and liquid dispenser 42 includes a dispenser pointer 48.

Liquid remover 40 may be any suitable device that removes liquid disposed outwardly from the surface of eye 22 in any suitable manner. In certain embodiments, liquid remover 40 directs electromagnetic radiation and/or mechanical energy towards a liquid to remove the liquid. For example, liquid remover 40 may include an ultrasonic emitter that generates ultrasound waves to displace the liquid. As another example, liquid remover 40 may include an infrared emitter that generates infrared waves that dries the liquid. As another example, liquid remover 40 may include a laser source (e.g., the excimer laser used for ablation or a separate laser) that generates a laser beam that dries the liquid. As another example, liquid remover 40 may include a device (e.g., an ocular tonometer) that creates a puff of air that dries the liquid.

Remover pointer 46 directs liquid remover 40 to remove liquid at a particular location of the surface of eye 22. In certain embodiments, remover pointer 46 may comprise an optical element or scanner that directs radiation and/or vibration towards a specific location of eye 22.

Liquid dispenser 42 may be any suitable device that applies liquid to the surface of eye 22 in any suitable manner. For example, liquid dispenser 42 may include a sprayer that sprays the liquid onto the surface. As another example, liquid dispenser 42 may include a cannula that targets the liquid onto a specific area of the surface. Features of liquid dispenser 42 may be adjusted to change, e.g., the direction, force, and/or spread of the application of the liquid.

Dispenser pointer 48 directs liquid dispenser 42 to apply liquid at a particular location of the surface of eye 22. In certain embodiments, dispenser pointer 48 may comprise a cylindrical component that directs the liquid towards a specific location of eye 22.

Figure 3:
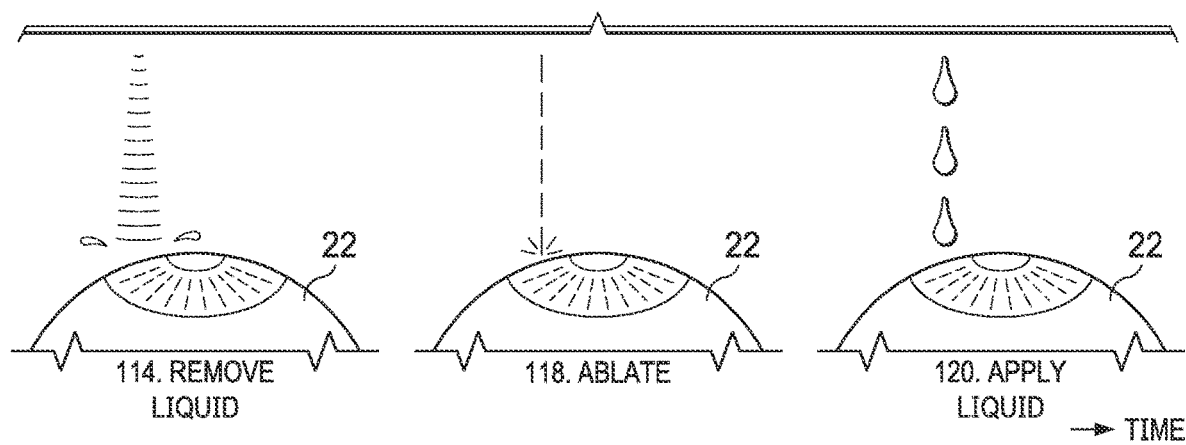
FIG. 3 illustrates an example of a method for managing appropriate moisture conditions during ophthalmic surgery that may be used by the system of FIG. 1.
Figure 4:
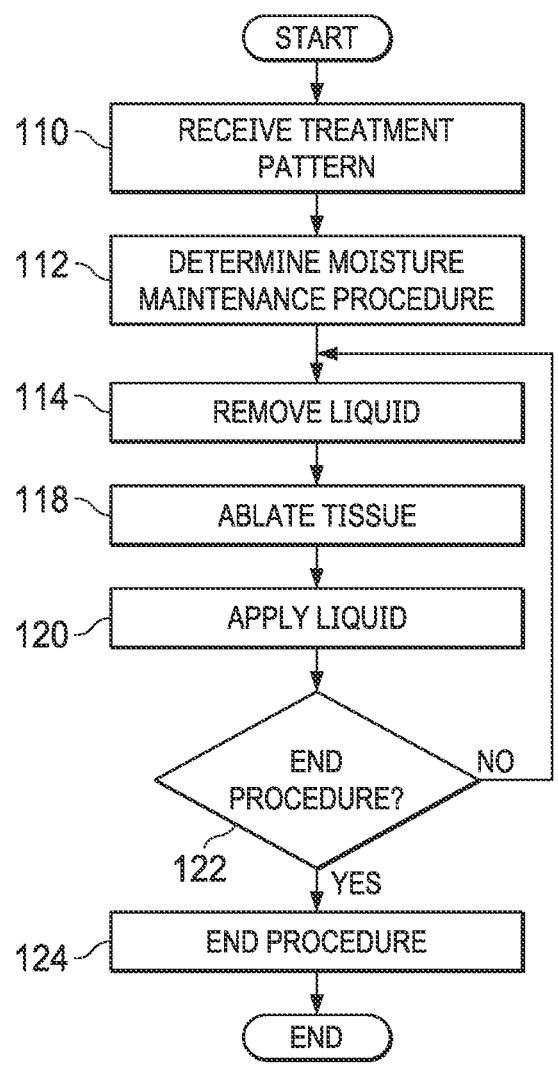
FIG. 4 illustrates an example of a method for managing appropriate moisture conditions during ophthalmic surgery that may be used by the system of FIG. 1.

FIGS. 3 and 4 illustrate an example of a method for managing appropriate moisture conditions during ophthalmic surgery that may be used by system 10 of FIG. 1. The method starts at step 110, where computer 30 receives a treatment pattern to be used to treat eye 22 during an ophthalmic surgical procedure. Computer 30 determines a moisture maintenance procedure at step 112. Computer 30 may retrieve a stored moisture maintenance procedure or may determine the procedure from the treatment pattern.

Computer 30 instructs liquid remover 40, laser device 15, and liquid dispenser 42 to perform steps 114 and 120. Liquid remover 40 removes liquid disposed outwardly from a location of eye 22 at step 114 according to the moisture maintenance procedure. Laser device 15 ablates the tissue of eye at the location at step 118 according to the treatment pattern. Liquid dispenser 42 applies more liquid to the location of eye 22 according to the moisture maintenance procedure at step 120.

The moisture maintenance procedure may be ending at step 122 according to the treatment pattern. If the procedure is not at the end, the method returns to step 114 to remove the liquid and continue the procedure. If the procedure is at the end, the method proceeds to step 124 to end the procedure. In certain embodiments, the last step of the moisture maintenance procedure may apply the liquid to most of or the entire laser ablation area. The method then ends.

A component (such as computer 30) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic laser ablation system comprising:
   a laser device configured to direct laser radiation towards an eye, the laser radiation comprising at least a first shot and a second shot, to ablate tissue of the eye according to a treatment pattern;
   a liquid remover configured to remove liquid disposed outwardly from a surface of the tissue of the eye; and
   a computer configured to:
      determine a moisture maintenance procedure;
      instruct the liquid remover to remove the liquid disposed outwardly from the tissue at a location of the eye according to the moisture maintenance procedure by removing the liquid prior to the first shot and prior to the second shot; and
      instruct the laser device to ablate the tissue at the location of the eye according to the treatment pattern.

2. The ophthalmic laser ablation system of claim 1, wherein the at least the first shot includes a sequence of shots, and wherein the computer is further configured to instruct the liquid remover to remove the liquid prior to the sequence of shots.

3. The ophthalmic laser ablation system of claim 1, the liquid remover comprising an ultrasonic emitter configured to generate a plurality of ultrasound waves to displace the liquid.

4. The ophthalmic laser ablation system of claim 1, the liquid remover comprising a device configured to create a puff of air to dry the liquid.

5. The ophthalmic laser ablation system of claim 1, wherein determining the moisture maintenance procedure comprises:
   determining the moisture maintenance procedure from the treatment pattern.

6. The ophthalmic laser ablation system of claim 1:
   further comprising a liquid dispenser configured to apply liquid onto the surface of the tissue; and
   the computer further configured to:
      instruct the liquid dispenser to apply liquid onto the surface of the tissue at the location of the eye according to the moisture maintenance procedure.

7. An ophthalmic laser ablation system comprising:
   a laser device configured to direct laser radiation towards an eye as a plurality of shots to ablate tissue of the eye according to a treatment pattern;
   a liquid remover configured to remove liquid disposed outwardly from a surface of the tissue of the eye;
   a liquid dispenser configured to apply liquid onto the surface of the tissue; and
   a computer configured to:
      determine a moisture maintenance procedure;
      instruct the liquid remover to remove the liquid disposed outwardly from the surface of the tissue at a location of the eye according to the moisture maintenance procedure by removing the liquid prior to a sequence of shots of the plurality of shots;
      instruct the liquid dispenser to apply liquid onto the surface of the tissue at the location of the eye according to the moisture maintenance procedure by applying the liquid after the sequence of shots of the plurality of shots; and
      instruct the laser device to ablate the tissue at the location of the eye according to the treatment pattern.

8. The ophthalmic laser ablation system of claim 7, the liquid dispenser comprising a sprayer configured to spray liquid onto the surface of the tissue.

9. The ophthalmic laser ablation system of claim 7, wherein the computer is further configured to instruct the liquid dispenser to apply the liquid after each shot of the plurality of shots.

10. The ophthalmic laser ablation system of claim 7, wherein applying liquid onto the surface of the tissue at the location of the eye according to the moisture maintenance procedure comprises:
   applying a liquid with a strong cooling effect.

11. The ophthalmic laser ablation system of claim 7, wherein applying liquid onto the surface of the tissue at the location of the eye according to the moisture maintenance procedure comprises:
applying a liquid for wound healing.

12. A method for ophthalmic laser ablation, comprising:
directing, by a laser device, laser radiation towards an eye as a plurality of shots to ablate tissue of the eye according to a treatment pattern;
applying, by a liquid dispenser, liquid onto a surface of the tissue of the eye;
removing, by a liquid remover, the liquid disposed outwardly from the surface of the tissue of the eye; and
performing the following with a computer:
determining a moisture maintenance procedure;
instructing the liquid dispenser to apply the liquid onto the surface of the tissue at a location of the eye according to the moisture maintenance procedure by applying the liquid after a sequence of shots of the plurality of shots;
instructing the liquid remover to remove the liquid disposed outwardly from the surface of the tissue at the location of the eye according to the moisture maintenance procedure; and
instructing the laser device to ablate the tissue at the location of the eye according to the treatment pattern.

13. The method of claim 12, wherein determining the moisture maintenance procedure comprises:
determining the moisture maintenance procedure from the treatment pattern.

14. The method of claim 12, wherein applying the liquid onto the surface of the tissue at the location of the eye according to the moisture maintenance procedure comprises performing at least one of the following:
applying a liquid with a strong cooling effect; and
applying a liquid for wound healing.

* * * * *